United States Patent [19]

Wells

[11] Patent Number: 4,682,027

[45] Date of Patent: Jul. 21, 1987

[54] METHOD AND APPARATUS FOR SAMPLE CONFIRMATION IN GAS CHROMATOGRAPHY

[75] Inventor: Gregory J. Wells, Suisun, Calif.

[73] Assignee: Varian Associates, Inc., Palo Alto, Calif.

[21] Appl. No.: 856,721

[22] Filed: Apr. 25, 1986

[51] Int. Cl.[4] .......................................... H01J 49/38
[52] U.S. Cl. .................... 250/291; 250/281; 250/282; 364/498
[58] Field of Search ............... 250/291, 281, 282, 290; 364/498; 324/312

[56] References Cited

U.S. PATENT DOCUMENTS

| | | | |
|---|---|---|---|
| 3,390,265 | 6/1968 | Llewellyn | 250/291 |
| 3,461,381 | 8/1960 | Nelson et al. | 324/312 |
| 3,505,517 | 4/1970 | Llewellyn | 250/291 |
| 3,742,212 | 6/1973 | McIver | 250/291 |
| 3,937,955 | 2/1976 | Comisarow et al. | 250/283 |
| 4,365,303 | 12/1982 | Hannah et al. | 364/498 |
| 4,464,570 | 8/1984 | Allemann et al. | 250/291 |

OTHER PUBLICATIONS

"Capillary Gas Chromatography/Fourier Transform Mass Spectrometery"-Robt White et al, Anal. Chem. 1982, 54, 2443-7.

"Fourier Transform Ion Cyclotron Resonance Mass Spectrometry", Baykut et al, Trends in Anal. Chem., vol. 5, No. 2, 1986, pp. 43 et seq.

"Coupling of HPLC and NMR", Buddrus et al, Organic Magnetic Resonance, vol. 13, No. 2, 1980, pp. 153 et seq.

"Fourier Transform Mass Spectrometry", Robt McIver, Jr., Smrtivsn Laboratory, No. 1980, pp. 18 et seq.

Primary Examiner—Craig E. Church
Assistant Examiner—Jack I. Berman
Attorney, Agent, or Firm—Stanley Z. Cole; Gerald M. Fisher; David Schnapf

[57] ABSTRACT

A method and apparatus for use in gas chromatography for confirming the presence of compounds in the sample. By directly comparing the transient decay time domain signals of the sample and of known compounds as detected in an ion cyclotron resonance mass spectrometer connected to the chromatographic column, one is able to effect sample confirmation without the computer intensive processes of Fourier transformation and analysis of the resulting mass spectrum.

6 Claims, 2 Drawing Figures

METHOD AND APPARATUS FOR SAMPLE CONFIRMATION IN GAS CHROMATOGRAPHY

FIELD OF THE INVENTION

The claimed invention relates generally to the field of gas chromatography and more particularly to the means for detecting and identifying the chemical substances eluting from the chromatography column after separation using ion cyclotron resonance or similar techniques.

BACKGROUND OF THE INVENTION

Gas chromatography (GC) is a well known method of separating mixtures of chemical compounds. A sample mixture to be analyzed is introduced into a chromatography column. Separation of the mixture occurs because the components travel through the column at different rates, eluting at different times. The period of elution of a component is commonly referred to as a "peak." Capillary columns used in modern GC provide very high resolution in sample separation because they provide very narrow peaks, often as narrow as one second.

A variety of methods and devices are available for qualitatively and quantitatively detecting the sample components eluting from the column. It is often desireable to use a mass spectrometer as part of the detection apparatus because of its ability to accurately identify an extremely wide range of substances. One type of mass spectrometer relies on the principles of ion cyclotron resonance (ICR).

Typically an ICR device comprises a sample cell wherein the sample is ionized and subject to a unidirectional uniform magnetic field. An oscillating electric field having one or more frequency components is applied in a direction orthogonal to the magnetic field. From the well-known equation, $$(\omega B=)e/m \tag{1}$$

(where $\omega$ is the frequency of the oscillating field, B is the magnetic field strength and e/m is the charge-to-mass ratio of the ion), it is seen that ions will resonate at particular frequencies in a given magnetic field. The resonant ions will absorb the rf energy and will be accelerated in roughly circular planar orbits of increasing diameter perpendicular to the magnetic field. A signal current is then detected as resonant ions strike and/or induce currents in the detector electrodes. Examples of ICR devices are described in U.S. Pat. Nos. 3,390,265; 3,461,381; 3,742,212; 3,505,517; 3,937,955; and 4,464,570.

Since each species of ion resonates at a particular frequency, it is necessary to subject the sample to a range of frequencies to detect the various chemical species present. The simplest approach to accomplish this is to sweep a frequency generator through a range of frequencies. However, this approach takes too long to be useful in GC/ICR.

The technique utilized to date in GC/ICR for establishing the mass spectrum of the chemical species present in the sample consists of wide-band RF excitation followed by Fourier transformation (FT) of the resulting transient decay time domain signal into the frequency domain. This approach permits the excitation of all the ions at once, eliminating the need for a time-consuming frequency sweep. Once the FT has been made, it is a straightforward task to calculate the mass spectrum of the ions within the sample cell. Any given frequency peak corresponds to a particular ion in the sample cell at the time of excitation. Moreover, the magnitude of the frequency peak is a function of the quantity of the ion in the cell. To obtain quantitative information about a particular chromatographic peak, it is necessary to integrate the detector response a multitude of times during the elution of the peak. In practical terms, at least 10 points are necessary for reasonably accurate integration.

In practice it has been found that the transient decays in the time domain should be digitized at twice the maximum resonant frequency encountered in the sample to prevent aliasing and to provide good mass resolution. By straightforward calculation, it can be shown that in a magnetic field of one Telsa, a range of ions with mass between 20 and 600 atomic mass units (amu) exhibit resonant frequencies in the range of 768 KHz to 25.6 KHz.

After performing the FT analysis of the digitized time domain signal, the resulting mass spectrum must then be compared to the mass spectra of known standards to confirm the presence of particular substance. Both the FT calculation and the subsequent comparison to known standards are routinely performed by computer. These operations require extensive data manipulation and take a relatively long time making it difficult to provide a real time output signal. This is particularly a problem with gas capillary chromatography where the peaks are narrow making it very difficult to obtain a sufficient number of data points needed for accurate integration.

OBJECTS OF THE INVENTION

Accordingly, it is an object of this invention to provide a simple, low cost and rapid means to employ an ICR mass spectrometer, or similar impulse excited device producing a transient decay signal, in conjunction with the output of a gas chromatograph, for identifying and quantifying the components in the sample.

A further object of this invention is to provide a real time output signal from an ICR detector, or similar device which qualitatively and quantitatively characterize the GC output with improved signal-to-noise ratio.

Another object of this invention is to provide a reliable means for sample confirmation without the need to resort to FT methods and the attendant need for sophisticated and high speed computers and computer peripherals.

SUMMARY OF THE INVENTION

The present invention involves sample confirmation using ICR or similar means by direct correlation of time domain data of the transient decay response. By directly comparing the time domain signal output from the sample cell with time domain data from a known standard, one can utilize wide-band excitation but forego FT analysis, thereby eliminating the need for a high-speed, expensive, sophisticated computer. It is relatively easier to obtain and process a sufficient number of data points and provide real time integration of the component peaks eluting from the gas chromatograph. In adddition, this technique provides improved signal-to-noise ratio and eliminates the need to know the mass spectrum of the known sample. Other advantages and aspects of the invention will be obvious to those skilled in the art upon reading the following description.

DETAILED DESCRIPTION OF THE INVENTION

Figure 1:
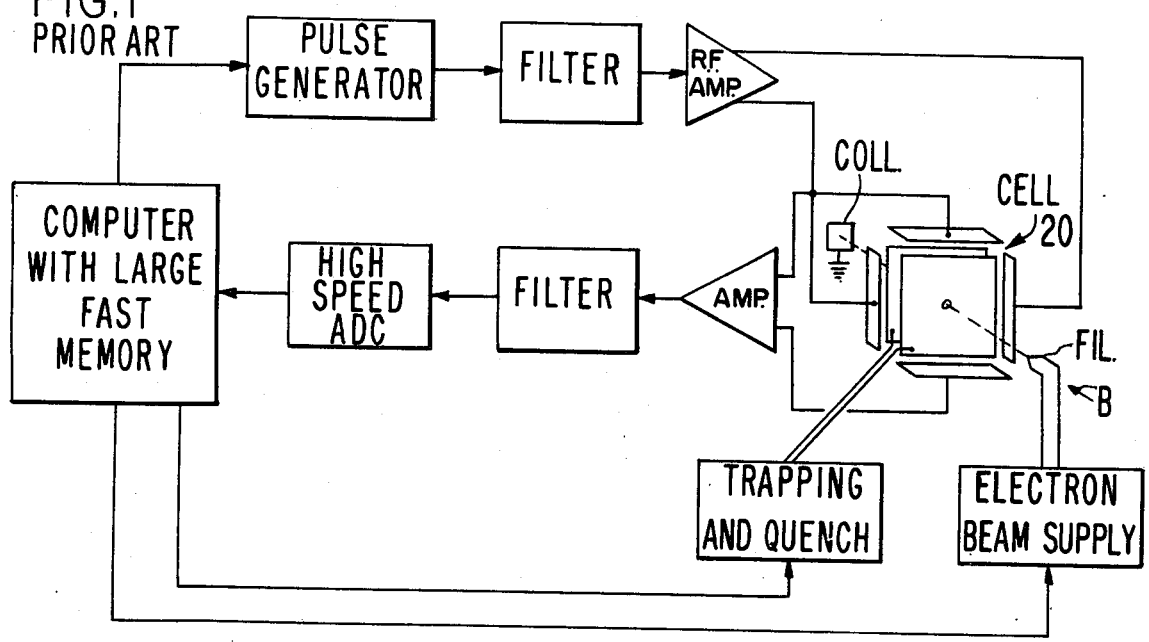
FIG. 1 is a block diagram of a pulsed ICR apparatus as known in the prior art.

FIG. 1 depicts an ICR sample analyzer of the prior art. A sample is introduced into a sample cell 20 located in a uniform magnetic field symbolically represented by the letter B in a direction depicted by the arrow. A pair of trapping and quenching electrodes are configured perpendicular to the magnetic field and two pairs of electrodes are configured perpendicular to each other and perpendicular to the first pair of electrodes so that the six electrodes form a generally rectangular box-shaped cell. The second and third pair of electrodes are used to apply a pulsed, wide-band RF signal perpendicular to the magnetic field and to detect the time domain signal response. A beam of electrons is emitted from a thermionic filament and directed into the cell to ionize the sample. Unabsorbed electrons pass through the cell and are attracted to a collector electrode.

The operation of a pulsed ICR mass spectrometer is well known. A quench pulse is first applied to the ICR cell to remove all ions. Next an ionizing beam of electrons is pulsed on for about 5 msec to form ions in the cell. The ions formed depend on the substances in the cell at the time of the electron beam pulse. By connecting the cell to the output of a GC the ions formed will depend on what is eluting from the column. A voltage pulse is then applied to the cell which has an amplitude, duration and shape such that it contains all frequencies required to excite the ions in the cell. The ions absorb the rf power from the pulse and induce currents in the end plates of the cell. These currents are amplified and filtered by conventional means and then digitized and stored.

Up to now GC/ICR has been used with FT analysis. Such analysis requires a high speed analog-to-digital converter (ADC) to digitize the time domain signal, and a fast computer with a large memory to perform a Fourier transformation into a frequency domain spectrum. Since frequency corresponds to mass, as described above, this can then readily be converted into a mass spectrum. Interpretation of the mass spectrum involve comparison with the mass spectra known chemical species which comparison also requires a sophisticated computer analysis.

The TD signal for a pulsed ICR is given by:

$$F(t) = \sum_{i=1}^{k} A_i \sin(\omega_i t + \phi_i) \exp(-t/\tau_i) \quad (2)$$

where $A_i, \omega_i$ and $\phi_i$ are the amplitude, frequency and phase of the ith ion that is excited by the rf pulse. The components of the TD are attenuated at any finite pressure by a damping term depending on $\tau_i$.

The process of gas chromatography separates the input sample mixture into its constituents. In general, only one or two chemical species (other than the carrier gas) will be present in the detector at any one time. In many applications the identity of a constituent may be surmised, albeit, not with a high level of confidence, from the length of time it takes to travel through the column and from knowledge of the original sample mixture. Even where uncertainty exists, in most cases the range of possibilities is small. Thus, often the major concern is simply confirmation that a peak is what is surmised. This confirmation can be accomplished, using the present invention, without the computer intensive step of FT analysis. Instead, the time domain data is directly correlated with data from known samples of the possible constituents.

When the time domain data is digitized using n points, the result can be viewed as a vector of dimension n given by the equation:

$$\vec{A} = \sum_{i=1}^{n} a_i t_i \quad (3)$$

where $a_i$ is the amplitude of the time domain signal at time $t_i$.

A normalizing constant $N_a$, directly related to the total number of ions that have been excited by the RF pulse, can be defined by the following equation:

$$N_a = \left( \sum_{i=1}^{n} a_i^2 \right)^{\frac{1}{2}} \quad (4)$$

The normalized vector A, which will be referred to as A', is then shown by the equation:

$$\vec{A'} = \sum_{i=1}^{n} a_i t_i / N_a \quad (5)$$

A graph of $N_a$ vs. time during the elution of a sample peak would yield a curve quantitatively showing the sample output. Such a curve would look similar, for example, to the output curve yielded by a flame ionization detector.

While the complete time domain signal contains the same amount of information as the complete frequency domain signal, a single point in the time domain is "richer" in information than the frequency domain signal generated after FT analysis. Any one point in time contains some information about all of the ions excited by the RF pulse. Each ion contributes, on the average, an amount weighted by its abundance. This is in contrast to a single digitized point of a conventional FT mass spectrum, which at most will contain information about ions of only one mass. More likely, the point will contain no information since no ions will be present at most masses. Accordingly, the dimension of the vector (i.e., the number of points of the time domain response that must be digitized) need not be large; in the range of 10 to 100 is quite adequate. Likewise, the sampling rate does not need to be as fast as for FT analysis.

Confirmation that an unknown eluent is the same as a known compound is accomplished by correlating their time domain "fingerprints." One way of doing this is by taking the inner product of the vector A' of the sample and the vector B', defined by the above equations and empirically established by digitizing time domain signal of the known compound. This inner product, referred to as correlation product P, is defined by the following equation:

$$P = \vec{A'} \cdot \vec{B'} = \frac{\left(\sum_{i=1}^{n} a_i b_i\right)}{N_a N_b} \quad (6)$$

where $N_b$ is likewise defined by equation (4). A perfect correlation between the sample A and the standard B would yield P=1; any mismatch would result in a P less than 1. It is noted that any aliasing which occurs would be a unique property of the substance and, thus, does not dictate the use of higher sampling rates because it does not affect the correlation product.

The correlation product given in equation 6 is the preferred method when the background due to column bleed or other sources of sample contamination is not important.

In the event that the time domain signal contains information that is not unique to the sample, due to the presence, for example, of background ions, the correlation product will be diluted to less than 1, creating uncertainty as to the confirmation. However, this may be corrected. The damping term ($\tau_i$) of equation 2 depends on the properties of the particular ion as well as the total pressure in the trap. This term can be made a constant for a given ion over a broad concentration range by keeping the cell pressure constant. An open split interface is well known and has the property of maintaining a constant pressure at the exit of the chromatographic column and at the head of the interface tube. For a pump with a given pumping speed, the gas flow rate thru the interface tube will be constant; therefore the cell pressure will be constant. Thus as the sample concentration changes, only the $A_i$ term in equation 2 will change. This implies that background ions from column bleed can be removed from the TD signal by simple subtraction of the TD signal from a blank run obtained at the nominal retention time of the standard. For example, let $F_s(t)$ be the TD signal for the sample (unknown or standard) and $F_b(t)$ be the TD signal for the blank background (no sample). The background corrected TD, $F_c(t)$ is:

$$F_c(t) = F_s(t) - F_B(t) \quad (7)$$

$$= \sum_{i=1}^{k} A_i^s \sin(\omega_i t + \phi_i^s) \exp(-t/\tau_i^s) -$$

$$\sum_{i=1}^{k} A_i^B \sin(\omega_i t + \phi_i^B) \exp(-t/\tau_i^B)$$

By using the same excitation pulse sequence for the blank, standard, and unknown; and by keeping the cell pressure constant ($\tau_i$ constant) equation 7 reduces to:

$$F_c(t) = \sum_{i}^{k} [A_i^s - A_i^B] \sin(\omega_i t + \phi_i) \exp(-t/\tau_i) \quad (8)$$

Or, in the notation of equation 4:

$$\vec{A'} = \sum_{i=1}^{n} [a_i^s - a_i^B] t_i / N_a \quad (9)$$

The procedure is to store a background TD vector acquired from a blank run at the retention time of the standard. Next, a TD vector of the standard is stored. The background corrected TD vector of the standard is formed by simple subtraction of the vector components and normalized as in equation 9. The background corrected unknown TD vector (B) is acquired and background corrected in a similar manner and the correlation product calculated as in equation 6.

The responses of the various ions likely to be introduced into the detector cell can be weighted by controlling the composition of the RF excitation pulse. This pulse may be seen as being composed of a summation of frequencies of various amplitudes. Adjusting the frequencies, and their amplitudes, present in the excitation pulse provides the means to accomplish weighting. Likewise, this approach can be used to minimize or eliminate the response of unwanted background ions.

In view of the foregoing, it is clear that the present invention has the following advantages over the prior art:

1. The fingerprint of the sample compound requires no knowledge of the mass spectrum of the sample, only a standard of the compound is needed;
2. FT analysis not necessary. Data acquisition rates and memory requirements may therefore be greatly reduced;
3. The correlation products require only simple sums and products of a low number of points;
4. All ions can contribute to the time domain signal for improved signal-to-noise ratio; and
5. The rate at which the correlation product can be obtained during the elution of a peak can be 10 to 30 Hertz which provides enough points to allow the peak to be quantified in real time.

Figure 2:
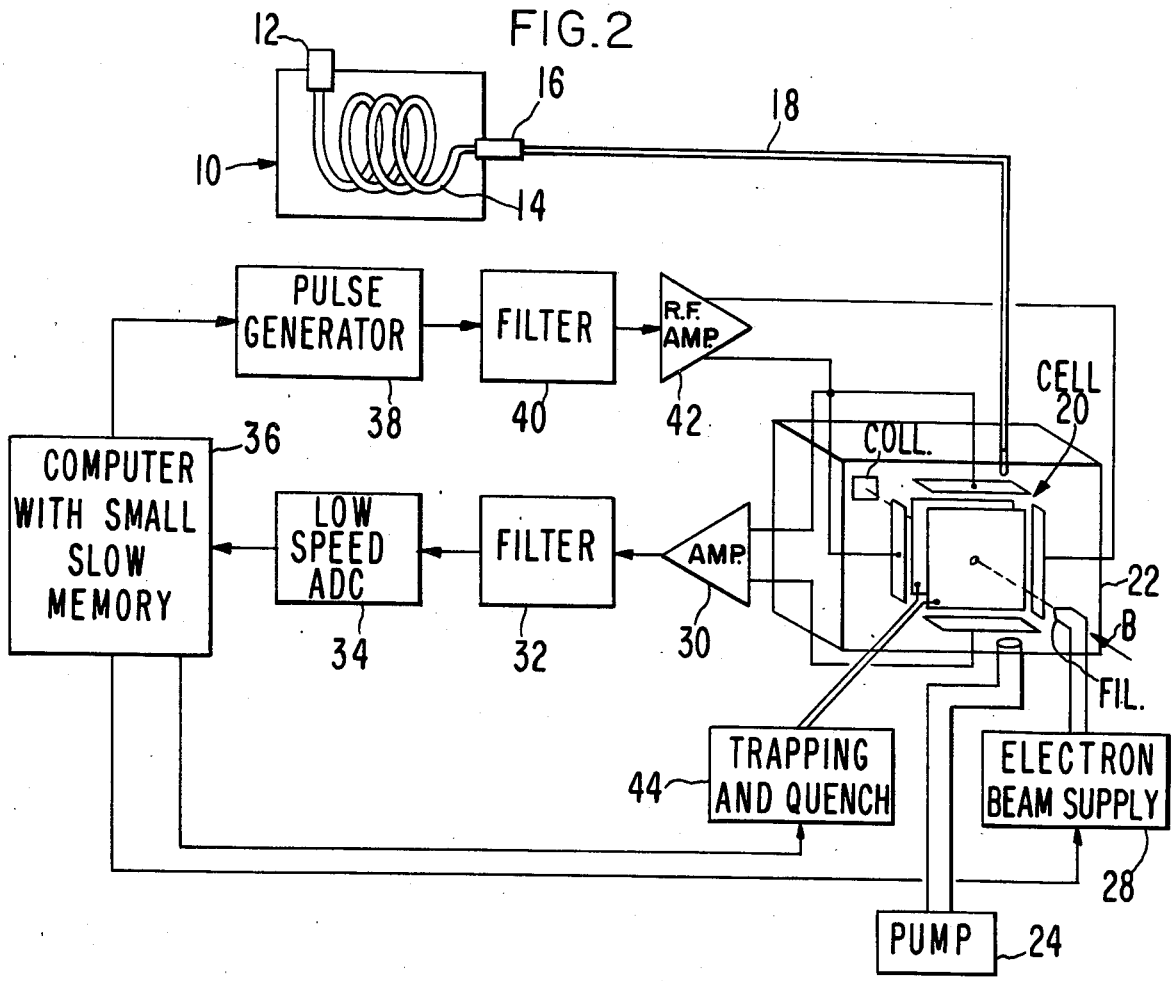
FIG. 2 is a block diagram of the apparatus of the present invention.

FIG. 2 shows the apparatus for practicing the present invention. A gas chromatograph 10 having a sample input 12, a column 14 and an output 16 is connected by conduit 18 to an ICR cell 20. The cell is constructed and operated as in the prior art. Note, that the RF impulse from RF amplifier 42 may be controlled, as described above, to contain a desired mix of frequencies of desired amplitudes. ADC 34 may be relatively low speed for the reasons previously described. Likewise, computer 36 may be relatively smaller and slower than would be necessary if FT analysis were being performed. After analysis and correlation of time domain data by the computer, the output signal from the cell may be directed to a chart recorder, or similar device (not shown) well known in the art.

While the invention has been described in the context of ion cyclotron resonance, it will be readily understood that it is not so limited. Direct correlation of time domain signals will work equally well with any form of ion resonance excited by a pulse and resulting in a transient decay in the time domain.

What is claimed is:

1. Apparatus for analysis of a vapor sample comprising:
    a pulsed ion-cyclotron resonance device including:
    (a) a sample cell,
    (b) means for ionizing a portion of said vapor sample within said sample cell,
    (c) magnet means for creating a substantially uniform magnetic field within said sample cell,
    (d) means for exciting said ions with a pulsed, wideband rf field orthogonal to said magnetic field,
    (e) means for detecting the cyclotron resonance of the excited ions and for generating a signal in the time domain,
    (f) means for digitizing said time domain signal, and (g) means for directly comparing said digitized time domain signal with at least one reference time domain signal and quantifying the degree of correlation of said sample and reference signals.

2. The apparatus of claim 1 further comprising:
a gas chromatograph for processing the vapor sample before the vapor sample is introduced into said pulsed ion-cyclotron resonance device.

3. The apparatus of claim 2 wherein said means for exciting said ions with a pulsed wide-band rf field includes means to adjust the mix of the frequencies and the amplitudes of said frequencies contained in the rf pulse.

4. The apparatus of claim 2 further comprising means to periodically obtain and integrate the time domain signals whereby a sample peak can be quantified.

5. A method of analyzing a gas sample including the steps of
 (a) obtaining a time domain transient decay signal of a known substance in a pulsed ion-cyclotron resonance device,
 (b) obtaining a time domain transient decay signal of an unknown sample in a pulsed ion-cyclotron resonance device,
 (c) comparing the signal of the unknown sample to the signal of the known substance and quantifying the degree of correlation of the signals.

6. A method of analyzing a gas sample as in claim 5, wherein said time domain signals are obtained as digitized vectors, said vectors are normalized, and said degree of correlation is quantified by calculating the dot product of said normalized vectors.

* * * * *